(12) United States Patent
Strohmaier et al.

(10) Patent No.: US 8,545,799 B2
(45) Date of Patent: Oct. 1, 2013

(54) EMM-11, A SYNTHETIC CRYSTALLINE MICROPOROUS MATERIAL, ITS PREPARATION AND USE

(75) Inventors: Karl G. Strohmaier, Port Murray, NJ (US); Douglas L. Dorset, Milford, NJ (US); Gordon J. Kennedy, Washington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/418,216

(22) Filed: Mar. 12, 2012

(65) Prior Publication Data

US 2012/0160773 A1   Jun. 28, 2012

Related U.S. Application Data

(62) Division of application No. 12/542,493, filed on Aug. 17, 2009, now Pat. No. 8,163,268.

(60) Provisional application No. 61/101,018, filed on Sep. 29, 2008.

(51) Int. Cl.
*C01B 33/36* (2006.01)
*C01B 39/00* (2006.01)

(52) U.S. Cl.
USPC .......................... 423/700; 423/702; 423/718

(58) Field of Classification Search
None
See application file for complete search history.

(56) References Cited

U.S. PATENT DOCUMENTS

| | | |
|---|---|---|
| 2,882,243 A | 4/1959 | Milton |
| 2,882,244 A | 4/1959 | Milton |
| 3,130,007 A | 4/1964 | Breck |
| 3,247,195 A | 4/1966 | Kerr |
| 3,314,752 A | 4/1967 | Kerr |
| 3,354,078 A | 11/1967 | Miale et al. |
| 3,702,886 A | 11/1972 | Argauer et al. |
| 3,709,979 A | 1/1973 | Chu |
| 3,832,449 A | 8/1974 | Rosinski et al. |
| 3,972,983 A | 8/1976 | Ciric |
| 4,016,245 A | 4/1977 | Plank et al. |
| 4,076,842 A | 2/1978 | Plank et al. |
| 4,954,325 A | 9/1990 | Rubin et al. |
| 4,981,663 A | 1/1991 | Rubin |

FOREIGN PATENT DOCUMENTS

| | | |
|---|---|---|
| FR | 2 918 979 | 1/2009 |
| WO | WO 2009/024665 | 2/2009 |

OTHER PUBLICATIONS

M. Afeworki et al., "Synthesis and Characterization of a New Microporous Material. 1. Structure of Aluminophosphate EMM-3," Chem. Mater, 2006, vol. 18, No. 6, pp. 1697-1704 (XP002526650).
G. Cao et al., "Structure of an aluminophosphate EMM-8: a multi-technique approach," Acta Crystallographics Section B, 2007, vol. 63, No. 1, pp. 56-62 (XP002526651).

(Continued)

*Primary Examiner* — Curtis Mayes
*Assistant Examiner* — Bijay Saha
(74) *Attorney, Agent, or Firm* — Darryl M. Tyus

(57) ABSTRACT

EMM-11 is a novel synthetic crystalline microporous material having a single crystalline phase with a unique 3-dimensional channel system comprising three sets of channels, namely a first set comprising 10-ring channels, and a second set and third set comprising 8-ring channels, having a unique T-atom connectivity and X-ray diffraction pattern which identify it as a novel material, and may be prepared with an organic structure directing agent, preferably, 3-isopropyl-1-methyl-1H-imidazol-3-ium. EMM-11 may be used in organic compounds conversion and absorptive processes.

20 Claims, 4 Drawing Sheets

(56) References Cited

OTHER PUBLICATIONS

Y. Lorgouilloux et al., "IM-16: A new microporous germanosilicate with a novel framework topology containing *d4r* and *mtw* composite building units," Journal of Solid State Chemistry, 2009, vol. 182, pp. 622-629.

Sastre et al., "ZeoTsites: a code for topological and crystallographic tetrahedral sites analysis in zeolites and zeotypes", Microporous and Mesoporous Materials 43 (2001) pp. 27-40.

Tuel et al., "NMR Characterization and Rietveld Refinement of the Structure of Rehydrated $AlPO_4$-34", J. Phys. Chem. B (2000) 104, pp. 5697-5705.

Koller et al., "Five-Coordinate Silicon in High-Silica Zeolites", J. Am. Chem. Soc. (1999) 121, pp. 3368-3376.

Olson et al., "Chemical and Physical Properties of the ZSM-5 Substitutional Series", Journal of Catalysis 61, (1980) pp. 390-396.

Meier et al., "The Topology of Three-Dimensional 4-Connected Nets: Classification of Zeolite Framework Types Using Coordination Sequences", Journal of Solid State Chemistry, 27, (1979) pp. 349-355.

Miale et al., "Catalysis by Crystalline Aluminosilicates, IV. Attainable Catalytic Cracking Rate Constants, and Superactivity", Journal of Catalysis 6, (1966), pp. 278-287.

Weisz et al., "Superactive Crystalline Aluminosilicate Hydrocarbon Catalysts", Journal of Catalysis 4, (1965), pp. 527-529.

3-isopropyl-1-methyl-1*H*-imidazol-3-ium

EMM-11, A SYNTHETIC CRYSTALLINE MICROPOROUS MATERIAL, ITS PREPARATION AND USE

CROSS REFERENCE TO RELATED APPLICATIONS

This application is a divisional of U.S. patent application Ser. No. 12/542,493, filed Aug. 17, 2009, now U.S. Pat. No. 8,163,268, which claims the benefit of U.S. Provisional Patent Application No. 61/101,018, filed Sep. 29, 2008, the disclosures of which are incorporated herein by reference in their entirety.

FIELD OF THE INVENTION

This invention relates to a novel synthetic crystalline microporous material, EMM-11, and a method for its preparation. This invention also relates to the use of EMM-11 in organic conversion and absorptive processes.

BACKGROUND OF THE INVENTION

Zeolitic materials, both natural and synthetic, have been demonstrated in the past to have utility as adsorbent materials and to have catalytic properties for various types of hydrocarbon conversion reactions. Certain zeolitic materials are ordered, porous crystalline metallosilicates having a definite crystalline structure as determined by X-ray diffraction (hereinafter referred to as "XRD"), within which there are a large number of smaller cavities which may be interconnected by a number of still smaller channels or pores. These cavities and pores are uniform in size within a specific zeolitic material. Since the dimensions of these pores are such as to accept adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates and substituted silicates, in which the silicon is partially or completely replaced by other tetrahedral elements. These silicates may be described as a rigid three-dimensional framework of $SiO_4$ tetrahedra and optionally tetrahedra of a trivalent element oxide, e.g., $AlO_4$, in which the tetrahedra are cross-linked by the sharing of oxygen atoms whereby the ratio of the total trivalent element and silicon atoms to oxygen atoms is 1:2. The electrovalence of the tetrahedra containing the trivalent element is balanced by the inclusion in the crystal of a cation, for example an alkali metal or an alkaline earth metal cation. This may be expressed wherein the ratio of the trivalent element, e.g., aluminum, to the number of various cations, such as $Ca^{+2}$, $Sr^{+2}$, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11(U.S. Pat. No. 3,709,979); zeolite ZSM-12 (U.S. Pat. No. 3,832,449), zeolite ZSM-20 (U.S. Pat. No. 3,972,983); ZSM-35 (U.S. Pat. No. 4,016,245); zeolite ZSM-23 (U.S. Pat. No. 4,076,842); zeolite MCM-22 (U.S. Pat. No. 4,954,325); and zeolite MCM-35 (U.S. Pat. No. 4,981,663), to name merely a few.

There are currently over 179 known microporous framework structures as tabulated by the International Zeolite Association. There exists the need for new structures, having different properties than those of known materials, for improving the performance of many organic compound conversion and absorption processes. Each structure has unique pore, channel and cage dimensions, which gives its particular properties as described above. EMM-11 is a new synthetic porous crystalline material having a unique framework structure and utility in such organic compound conversion and absorption processes.

SUMMARY OF THE INVENTION

EMM-11 is a novel synthetic crystalline microporous material having a single crystalline phase with a unique 3-dimensional channel system comprising three intersecting sets of channels; namely, a first set comprising 10-ring channels, a second set and a third set comprising 8-ring channels.

In one or more embodiments, EMM-11 is defined by the connectivity between the tetrahedrally-coordinated atoms in its framework. In one or more embodiments, the connectivity between tetrahedrally-coordinated atoms in the unit cell of EMM-11 is substantially as set forth in Table I.

In one or more embodiments, EMM-11, in as-synthesized form, has a composition of:

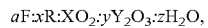

$aF:xR:XO_2:yY_2O_3:zH_2O$, wherein F is fluorine; R is an organic compound; preferably an organic structure directing agent (SDA); more preferably, the organic SDA comprises 3-isopropyl-1-methyl-1H-imidazol-3-ium; X is one or more elements capable of tetrahedral coordination; preferably, one or more such elements selected from the group consisting of Li, Be, P, Si, Ge, Zn, Cr, Mg, Co, Ni, Mn, As, In, Cu, Sn, Sb, Ti, and Zr; more preferably, one or more tetravalent elements selected from the group consisting of Si, Ge, and Ti; Y is one or more trivalent elements capable of tetrahedral coordination; preferably one or more trivalent elements selected from the group consisting of B, Al, Fe, and Ga; O and H are oxygen and hydrogen, respectively; a is a number having a value in the range of greater than or equal to 0 to less than or equal to 0.4; x is a number having a value in the range of greater than or equal to or equal to 0 to less than or equal to 0.4; y is a number having a value in the range of greater than or equal to or equal to 0 to less than or equal to 0.2; and z is a number having a value in the range of greater than or equal to 0 to less than or equal to 20.

In one embodiment, the EMM-11 structure, in as-synthesized form, may be defined by the X-ray diffraction pattern including values as substantially as set forth in Table 4.

In one or more embodiments, EMM-11, in calcined form, has a composition of:

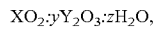

$XO_2:yY_2O_3:zH_2O$, wherein X is one or more elements capable of tetrahedral coordination; preferably, one or more elements selected from the group consisting of Li, Be, P, Si, Ge, Zn, Cr, Mg, Co, Ni, Mn, As, In, Cu, Sn, Sb, Ti, and Zr; more preferably, one or more tetravalent elements selected from the group consisting of Si, Ge, and Ti; Y is one or more trivalent elements capable of tetrahedral coordination; preferably one or more trivalent elements selected from the group consisting of B, Al, Fe, and Ga; O and H are oxygen and hydrogen, respectively; y is a number having a value in the range of greater than or equal to 0 to less than or equal to 0.2; and z is a number having a value in the range of greater than or equal to 0 to less than or equal to 20.

In one embodiment, the EMM-11 structure, in calcined form, may be defined by the XRD pattern including values substantially as set forth in Table 5.

BRIEF DESCRIPTION OF THE DRAWINGS

FIG. 1 shows the structural projections of the three sets of channels for EMM-11.

DETAILED DESCRIPTION OF THE INVENTION

Framework Structure

Figure 1A:
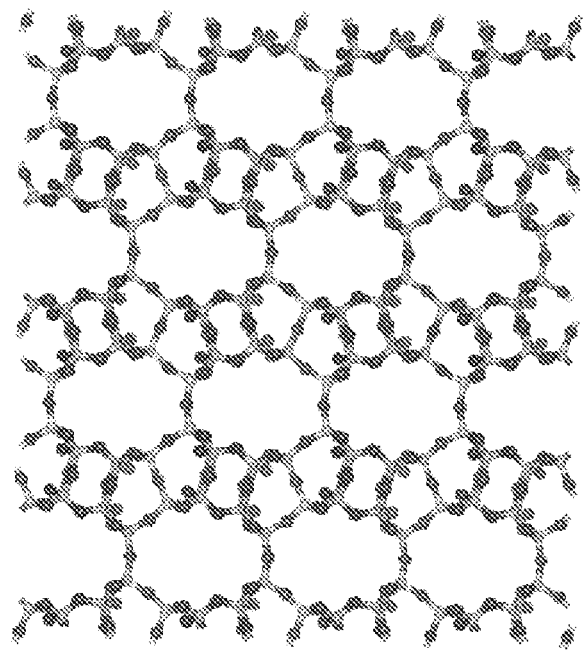
FIG. 1A shows the 10-ring channel.
Figure 1B:
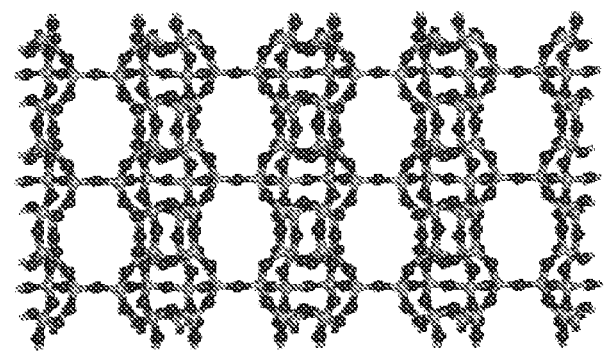
FIGS. 1B and 1C show the 8-ring channels.
Figure 1C:
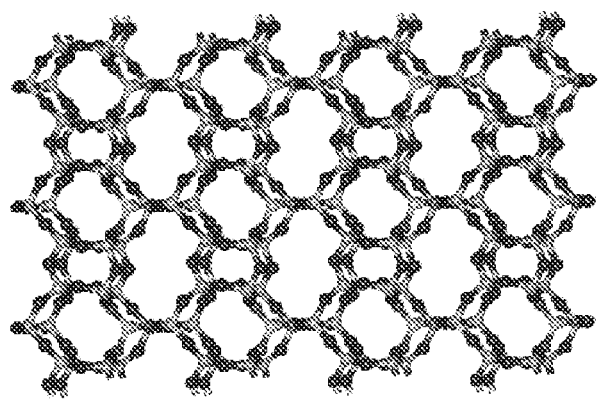

The synthetic crystalline microporous material of the present invention, EMM-11, has a single crystalline phase with a unique 3-dimensional channel system comprising three sets of channels. The first set comprises 10-ring channels (FIG. 1A). The second set and third set comprise 8-ring channels (FIGS. 1B and 1C).

In a preferred embodiment, EMM-11 comprises a first set of generally parallel channels each of which is defined by a 10-membered ring of tetrahedrally-coordinated atoms; a second set of generally parallel channels which are defined by 8-membered rings of tetrahedrally-coordinated atoms and which are orthogonal to and intersect with the channels of the first set; and a third set of generally parallel channels which intersect with the channels of said first and second sets and each of which is defined by a 8-membered ring of tetrahedrally-coordinated atoms. The first set of 10-ring channels each has cross-sectional dimensions of about 6.2 Angstroms by about 3.9 Angstroms. The second set of 8-ring channels each has cross-sectional dimensions of about 4.8 Angstroms by about 3.3 Angstroms. The third set of 8-ring channels each has cross-sectional dimensions of about 4.8 Angstroms by about 2.1 Angstroms.

In one or more embodiments, EMM-11 is defined by the connectivity between the tetrahedrally-coordinated atoms in its framework. The connectivity between tetrahedrally-coordinated atoms (also referred to as "T-atoms") in the unit cell of EMM-11 is substantially as set forth in Table 1.

TABLE 1

EMM-11 Tetrahedrally-coordinated Atom Connectivity

| T-atom | Connected to: |
|---|---|
| T1 | T2, T6, T13, T17 |
| T2 | T1, T5, T14, T18 |
| T3 | T4, T8, T15, T19 |
| T4 | T3, T7, T16, T20 |
| T5 | T2, T6, T9, T21 |
| T6 | T1, T5, T10, T22 |
| T7 | T4, T8, T11, T23 |
| T8 | T3, T7, T12, T24 |
| T9 | T5, T10, T14, T21 |
| T10 | T6, T9, T13, T22 |
| T11 | T7, T12, T16, T23 |
| T12 | T8, T11, T15, T24 |
| T13 | T1, T10, T14, T17 |
| T14 | T2, T9, T13, T18 |
| T15 | T3, T12, T16, T19 |
| T16 | T4, T11, T15, T20 |
| T17 | T1, T13, T18, T21 |
| T18 | T2, T14, T17, T20 |
| T19 | T3, T15, T20, T23 |
| T20 | T4, T16, T18, T19 |
| T21 | T5, T9, T17, T22 |
| T22 | T6, T10, T21, T24 |
| T23 | T7, T11, T19, T24 |
| T24 | T8, T12, T22, T23 |

Tetrahedrally-coordinated atoms are those capable of having tetrahedral coordination, including one or more of, but not limited to, boron (B), lithium (Li), beryllium (Be), aluminum (Al), phosphorous (P), silicon (Si), gallium (Ga), germanium (Ge), zinc (Zn), chromium (Cr), magnesium (Mg), iron (Fe), cobalt (Co), nickel (Ni), manganese (Mn), arsenic (As), indium (In), copper (Cu), tin (Sn), antimony (Sb), titanium (Ti) and zirconium (Zr).

Bridging atoms are those capable of connecting two tetrahedrally-coordinated atoms, examples including one or more of, but not limited to, oxygen (O), nitrogen (N), fluorine (F), sulfur (S), selenium (Se), and carbon (C).

The complete structure of EMM-11 is built by connecting multiple unit cells as defined above in a fully-connected three-dimensional framework. The tetrahedrally-coordinated atoms in one unit cell are connected to certain tetrahedrally-coordinated atoms in all of its adjacent unit cells. While Table 1 lists the connections of all the tetrahedrally-coordinated atoms for a given unit cell of EMM-11, the connections may not be to the particular atom in the same unit cell but to an adjacent unit cell. All of the connections listed in Table 1 are such that they are to the closest tetrahedrally-coordinated atoms, irrespective of whether they are in the same unit cell or in adjacent unit cells.

Figure 2:
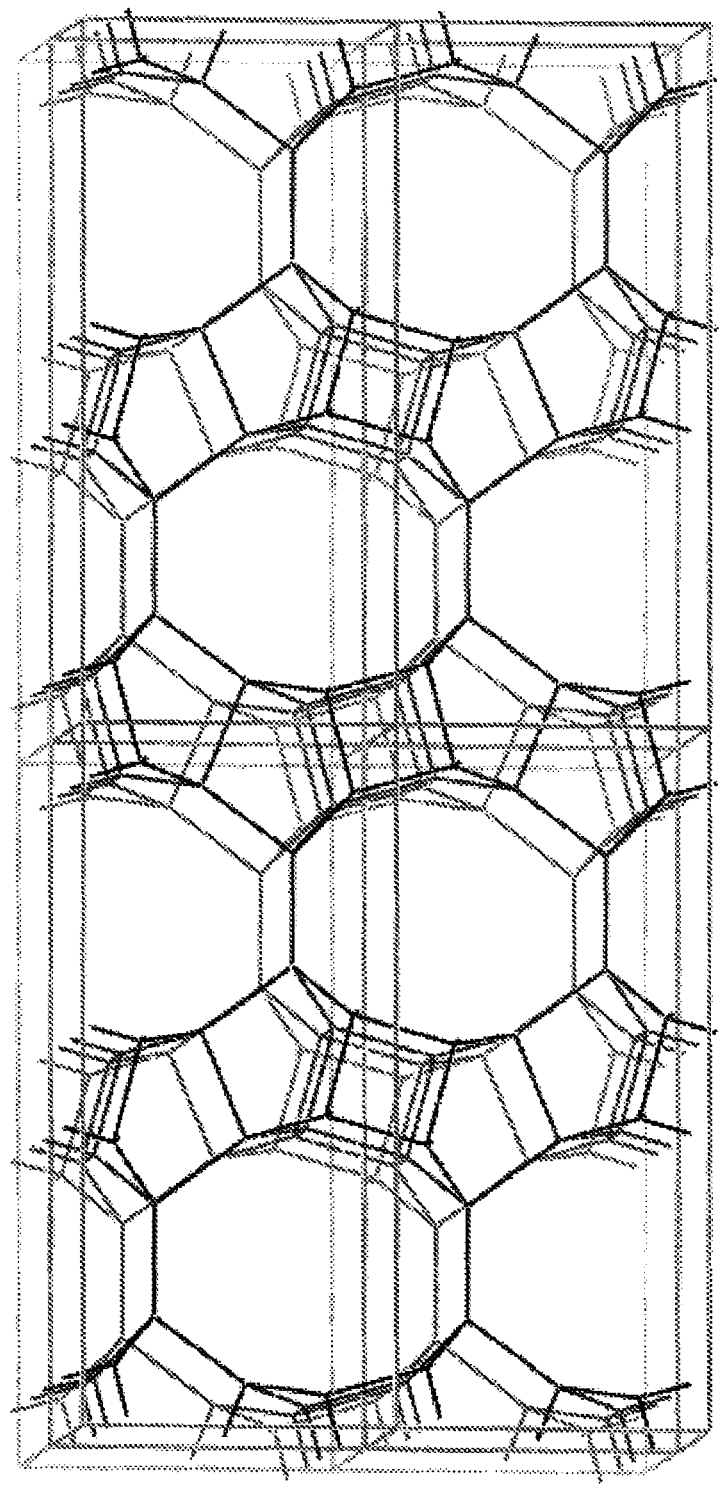
FIG. 2 displays the framework structure of the tetrahedrally-coordinated atoms for EMM-11. There are eight unit cells the edges of which are defined by the box shown.

The pore structure of one or more embodiments of EMM-11 may be displayed by its unit cell. The unit cell is the smallest repeating unit containing all the structural elements of a material. The pore structure of EMM-11 is illustrated in FIG. 2 (which shows only the tetrahedrally-coordinated atoms) down the direction of the straight 10-membered ring channels. There are eight unit cells in FIG. 2, whose limits are defined by the box shown.

The structure of one or more embodiments of EMM-11 may also be defined by the x, y, z (Cartesian) coordinates of the position of each tetrahedrally-coordinated atom in the unit cell. Each tetrahedrally-coordinated atom is bonded to bridging atoms, which are also bonded to adjacent tetrahedrally-coordinated atoms. Since tetrahedrally-coordinated atoms may move about due to other crystal forces (due to the presence of inorganic or organic species, for example), or by the choice of tetrahedrally-coordinated and bridging atoms, a range of ±1.00 Angstroms is implied for the x coordinate positions and a range of ±0.50 Angstroms for the y and z coordinate positions. The approximate x, y, z coordinate positions of tetrahedrally-coordinated atoms (T-atoms) for the EMM-11 in units of Angstroms that are typical when T=silicon and the bridging atoms are oxygen are substantially as set forth in Table 2.

TABLE 2

Coordinate Positions of T-atoms

| T-atom | x (Angstroms) | y (Angstroms) | z (Angstroms) |
|---|---|---|---|
| T1  | 1.027 ± 1.00  | 1.469 ± 0.50 | 7.056 ± 0.50 |
| T2  | 1.817 ± 1.00  | 1.469 ± 0.50 | 1.044 ± 0.50 |
| T3  | 8.864 ± 1.00  | 6.032 ± 0.50 | 7.056 ± 0.50 |
| T4  | 8.074 ± 1.00  | 6.032 ± 0.50 | 1.044 ± 0.50 |
| T5  | 18.756 ± 1.00 | 1.469 ± 0.50 | 1.816 ± 0.50 |
| T6  | 17.966 ± 1.00 | 1.469 ± 0.50 | 7.828 ± 0.50 |
| T7  | 10.918 ± 1.00 | 6.032 ± 0.50 | 1.816 ± 0.50 |
| T8  | 11.708 ± 1.00 | 6.032 ± 0.50 | 7.828 ± 0.50 |
| T9  | 18.756 ± 1.00 | 6.032 ± 0.50 | 1.816 ± 0.50 |
| T10 | 17.966 ± 1.00 | 6.032 ± 0.50 | 7.828 ± 0.50 |
| T11 | 10.918 ± 1.00 | 1.469 ± 0.50 | 1.816 ± 0.50 |
| T12 | 11.708 ± 1.00 | 1.469 ± 0.50 | 7.828 ± 0.50 |
| T13 | 1.027 ± 1.00  | 6.032 ± 0.50 | 7.056 ± 0.50 |
| T14 | 1.817 ± 1.00  | 6.032 ± 0.50 | 1.044 ± 0.50 |
| T15 | 8.864 ± 1.00  | 1.469 ± 0.50 | 7.056 ± 0.50 |
| T16 | 8.074 ± 1.00  | 1.469 ± 0.50 | 1.044 ± 0.50 |
| T17 | 1.486 ± 1.00  | 3.751 ± 0.50 | 5.061 ± 0.50 |
| T18 | 3.352 ± 1.00  | 3.751 ± 0.50 | 2.482 ± 0.50 |
| T19 | 8.405 ± 1.00  | 3.751 ± 0.50 | 5.061 ± 0.50 |
| T20 | 6.540 ± 1.00  | 3.751 ± 0.50 | 2.482 ± 0.50 |
| T21 | 18.296 ± 1.00 | 3.751 ± 0.50 | 3.810 ± 0.50 |
| T22 | 16.431 ± 1.00 | 3.751 ± 0.50 | 6.390 ± 0.50 |
| T23 | 11.378 ± 1.00 | 3.751 ± 0.50 | 3.810 ± 0.50 |
| T24 | 13.243 ± 1.00 | 3.751 ± 0.50 | 6.390 ± 0.50 |

Although the x, y, z Cartesian coordinates given in Table 2 may accurately reflect the positions of tetrahedrally-coordinated atoms in an idealized structure, the true structure may be more accurately described by the connectivity between the framework atoms as shown in Table 1.

Still another way to describe this connectivity of the tetrahedrally-coordinated atoms is by the use of coordination sequences as applied to microporous frameworks by W. M. Meier and H. J. Moeck, in the *Journal of Solid State Chemistry* 27, p. 349 (1979). In a microporous framework, each tetrahedrally-coordinated atom, $N_0$, is connected to $N_1=4$ neighboring tetrahedrally-coordinated atoms through bridging atoms (typically oxygen). These neighboring tetrahedrally-coordinated atoms are then connected to $N_2$ tetrahedrally-coordinated atoms in the next shell. The $N_2$ atoms in the second shell are connected to $N_3$ tetrahedrally-coordinated atoms in the third shell, and so on. Each tetrahedrally-coordinated atom is only counted once, such that, for example, if a tetrahedrally-coordinated atom is in a 4-membered ring, at the fourth shell the $N_0$ atom is not counted second time, and so on. Using this methodology, a coordination sequence may be determined for each unique tetrahedrally-coordinated atoms of a 4-connected net of tetrahedrally-coordinated atoms. The following line lists the maximum number of tetrahedrally-coordinated atoms for each shell.

$$N_0=1 \; N_1 \leq 4 \; N_2 \leq 12 \; N_3 \leq 36 \; N_k \leq 4 \cdot 3^{k-1}$$

The coordination sequence for the EMM-11 structure is given in Table 3. The tetrahedrally-coordinated atoms connectivity as listed in Table 1 and is for tetrahedrally-coordinated atoms only. Bridging atoms, such as oxygen usually connects the tetrahedrally-coordinated atoms. Although most of the tetrahedrally-coordinated atoms are connected to other tetrahedrally-coordinated atoms through bridging atoms, it is recognized that in a particular crystal of a material having a framework structure, it is possible that a number of tetrahedrally-coordinated atoms may not connected to one another. Reasons for non-connectivity include, but are not limited by tetrahedrally-coordinated atoms located at the edges of the crystals and by defects sites caused by, for example, vacancies in the crystal. The framework listed in Table 1 and Table 3 is not limited in any way by its composition, unit cell dimensions or space group symmetry.

TABLE 3

Coordination Sequence for EMM-11 Structure

| T-atom Type | Label | Coordination Sequence | | | | | | | | | | | | |
|---|---|---|---|---|---|---|---|---|---|---|---|---|---|---|
| 1 | T1  | 4 | 9  | 18 | 34 | 60 | 87 | 107 | 132 | 181 | 238 | 276 | 313 | 377 |
| 2 | T2  | 4 | 9  | 18 | 36 | 60 | 84 | 106 | 135 | 181 | 235 | 278 | 318 | 376 |
| 3 | T17 | 4 | 12 | 21 | 33 | 54 | 83 | 116 | 151 | 181 | 220 | 275 | 331 | 383 |
| 4 | T18 | 4 | 12 | 25 | 37 | 51 | 79 | 117 | 152 | 182 | 220 | 275 | 337 | 390 |

One way to determine the coordination sequence for a given structure is from the atomic coordinates of the framework atoms using the computer program zeoTsites (see G. Sastre, J. D. Gale, *Microporous and Mesoporous Materials* 43, p. 27 (2001).

While the idealized structure contains only 4-coordinate tetrahedrally-coordinated atoms, it is possible under certain conditions that some of the framework atoms may be 5- or 6-coordinate. This may occur, for example, under conditions of hydration when the composition of the material contains mainly phosphorous and aluminum tetrahedrally-coordinated atoms. When this occurs it is found that tetrahedrally-coordinated atoms may be also coordinated to one or two oxygen atoms of water molecules (—OH$_2$), or of hydroxyl groups (—OH). For example, the molecular sieve AlPO$_4$-34 is known to reversibly change the coordination of some aluminum tetrahedrally-coordinated atoms from 4-coordinate to 5- and 6-coordinate upon hydration as described by A. Tuel et al. in *J. Phys. Chem. B* 104, p. 5697 (2000). It is also possible that some framework tetrahedrally-coordinated atoms may be coordinated to fluorine atoms (—F) when materials are prepared in the presence of fluorine to make materials with 5-coordinate tetrahedrally-coordinated atoms as described by H. Koller in *J. Am. Chem Soc.* 121, p. 3368 (1999).

XRD Patterns

In one embodiment, the as-synthesized form of EMM-11 has a characteristic XRD pattern, the essential reflection lines of which are substantially as set forth in Table 4. Variations occur as a function of the specific composition and its loading in the structure. For this reason the intensities and d-spacing are given as ranges.

TABLE 4

XRD Reflection Lines for EMM-11 in As-synthesized Form

| d-spacing (Angstroms) | Relative Intensity |
|---|---|
| 10.1-9.9 | 60-100 |
| 9.20-9.01 | 5-50 |
| 5.86-5.78 | 5-50 |
| 5.05-5.00 | 5-50 |
| 3.79-3.76 | 20-70 |
| 3.77-3.74 | 20-70 |
| 3.65-3.62 | 30-80 |
| 3.54-3.51 | 30-80 |
| 3.51-3.49 | 20-70 |
| 3.32-3.29 | 5-50 |
| 2.552-2.538 | 5-50 |

The EMM-11 material of the present invention may be calcined to remove the organic SDA, any fluorine, and water, without loss of crystallinity. This is useful for activating the material for subsequent absorption of other guest molecules such as hydrocarbons.

In one embodiment, the calcined form of EMM-11 has a characteristic XRD pattern the essential reflection lines of which are substantially as set forth in Table 5. Variations occur as a function of specific composition, temperature and the level of hydration in the structure. For this reason the intensities and d-spacing are given as ranges.

TABLE 5

XRD Reflection Lines for EMM-11 in Calcined Form

| d-spacing (Angstroms) | Relative Intensity |
|---|---|
| 10.0-9.8 | 60-100 |
| 8.17-8.02 | 1-20 |
| 5.77-5.69 | 1-20 |
| 5.00-4.94 | 5-40 |
| 3.70-3.67 | 5-40 |
| 3.65-3.62 | 5-40 |
| 3.47-3.45 | 1-20 |
| 3.32-3.29 | 1-20 |
| 3.28-3.25 | 1-20 |
| 2.550-2.536 | 1-20 |

Variations in the X-ray diffraction pattern may occur between the different chemical compositional forms of EMM-11, such that the exact EMM-11 structure may vary due its particular composition and whether or not it has been calcined and rehydrated.

The XRD patterns in Table 4 and Table 5 were measured with Cu Kα radiation using a PANalytical X'Pert diffractometer with a X'celerator detector, Bragg-Brentano geometry, 45 kV and 40 mA tube voltage and current, 1/16° fixed divergence slit, 0.017° step size.

Composition

In one or more embodiments, EMM-11, in as-synthesized form, has a composition of:

$$aF:xR:XO_2:yY_2O_3:zH_2O,$$

wherein F is fluorine; R is an organic compound; preferably, an organic SDA, more preferably, the organic SDA comprises 3-isopropyl-1-methyl-1H-imidazol-3-ium. X is any element capable of tetrahedral coordination; preferably, one or more elements selected from the group consisting of Li, Be, P, Si, Ge, Zn, Cr, Mg, Co, Ni, Mn, As, In, Cu, Sn, Sb, Ti, and Zr. Y is any trivalent element capable of tetrahedral coordination; preferably, one or more elements selected from the group consisting of B, Al, Fe, and Ga. O and H are oxygen and hydrogen, respectively; O and H are oxygen and hydrogen, respectively; a is a number having a value in the range of greater than or equal to 0 to less than or equal to 0.4; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

In one or more embodiments, EMM-11, in calcined form, has a composition of:

$$XO_2:yY_2O_3:zH_2O,$$

wherein X is any tetravalent element capable of tetrahedral coordination; preferably, one or more elements selected from the group consisting of Li, Be, P, Si, Ge, Zn, Cr, Mg, Co, Ni, Mn, As, In, Cu, Sn, Sb, Ti, and Zr; more preferably, one or more elements selected from the group consisting of Si, Ge, and Ti; Y is any trivalent element capable of tetrahedral coordination; preferably one or more elements selected from the group consisting of B, Al, Fe, and Ga; O and H are oxygen and hydrogen, respectively; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

Method of Making EMM-11

In one embodiment, the invention includes a method of preparing the synthetic crystalline microporous material of EMM-11 comprising the steps of:

(a) forming a reaction mixture comprising at least one element having tetrahedrally-coordinated atom, at least one organic compound, and optionally at least one source of fluorine, wherein the at least one element having tetrahedrally-coordinated atoms is selected from the group consisting of B, Li, Be, Al, P, Si, Ga, Ge, Zn, Cr, Mg, Fe, Co, Ni, Mn, As, In, Cu, Sn, Sb, Ti, and Zr;

(b) maintaining the reaction mixture under suitable crystallization conditions effective to form crystals of the synthetic crystalline microporous material; and (c) recovering the crystals from the reaction mixture.

In one or more embodiments, the at least one element having tetrahedrally-coordinated atoms of the reaction mixture is tetravalent, or a combination of tetravalent and trivalent tetrahedrally-coordinated atoms.

Preferably, the trivalent element is selected from the group consisting of B, Al, Fe, and Ga.

In one or more embodiments, the organic compound is preferably an organic SDA; more preferably, the organic SDA comprises 3-isopropyl-1-methyl-1H-imidazol-3-ium.

In one or more embodiments, the reaction mixture may optionally comprise at least one source of fluoride.

Sources of silica may be colloidal, fumed or precipitated silica, silica gel, sodium or potassium silicates, or organic silicon such as tetraalkylorthosilicates, e.g. tetraethylorthosilicate, etc.

Sources of other tetravalent and trivalent elements capable of tetrahedral coordination include, but are not limited to, boric acid, germanium (IV) ethoxide, germanium oxide, germanium nitrate, aluminum nitrate, sodium aluminate, aluminum sulfate, aluminum hydroxide, aluminum chloride, iron nitrate, iron chloride, and gallium nitrate, etc. Sources of fluoride may be ammonium fluoride, hydrogen fluoride, hydrofluoric acid, and other suitable fluoride-containing compounds.

In one or more embodiments, the reaction mixture is heated to a temperature for a time sufficient to form crystals of the synthetic crystalline microporous material of this invention. The reaction mixture is maintained under suitable crystallization conditions, typically in sealed autoclaves.

Non-limiting suitable crystallization conditions include heating at a temperature between 95° C. and 250° C. for a time sufficient for crystallization to react at the temperature used, for example, from several hours up to 100 days; preferably from about 12 hours to about 30 days. Stirring or tumbling may be applied during crystallization.

The as-synthesized EMM-11 product may be conveniently recovered by filtration, centrifugation, or decanting of mother liquor followed by water washing. The washed EMM-11 may then be dried by heating to a temperature of at least about 100° C. for at least 1 minute and generally not longer than 48 hours. While subatmospheric pressure may be employed for the drying, atmospheric pressure is desired for reasons of convenience. It may then be subjected to subsequent processing steps well-known in the art to remove part or all of the water, fluorine and any organic constituent (e.g., an organic SDA).

After recovery, to the extent desired and depending on the $XO_2/Y_2O_3$ molar ratio of the material, any cations present in the as-synthesized EMM-11 may be replaced in accordance with techniques well known in the art by ion exchange with other cations. Preferred replacing cations include metal ions, hydrogen ions, and hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

When employed as a catalyst in an organic compound conversion process or as an adsorbent, EMM-11 should first be calcined to remove the organic SDA. If the EMM-11 is allowed to re-hydrate, it should then be dehydrated, at least partially. Calcination may be performed in an oxygen-containing atmosphere at a temperature up to about 927° C., preferably at about 540° C. Dehydration may be done by heating to a temperature in the range of 100° C. or higher in an atmosphere such as air, nitrogen, etc., and at atmospheric, subatmospheric or superatmospheric pressures for between 1 minutes and 48 hours. Dehydration may also be performed at room temperature merely by placing the EMM-11 in a vacuum, but a longer time is required to obtain a sufficient amount of dehydration.

The dehydrated catalyst is often combined with a binder and subjected to thermal treatment (e.g. calcination) which may be performed at a temperature up to about 927° C., preferably at about 540° C. The thermally-treated EMM-11, especially in its metal, hydrogen or ammonium forms, is particularly useful in the catalysis of certain organic, e.g., hydrocarbon, conversion reactions.

Use in Organic Conversion and Absorptive Processes

EMM-11 may be used to catalyze a wide variety of chemical conversion processes, particularly organic compound conversion and hydrocarbon processes, many of which have current commercial and/or industrial importance. In order to catalyze such chemical conversion processes, EMM-11 (either alone or in combination with other material) should possess acid activity.

A catalyst comprising EMM-11 may be used in organic conversion processes. In one embodiment, the invention includes a method for converting an organic compound comprising the step of contacting the organic compound with a catalyst comprising one or more embodiments of the synthetic crystalline microporous material of this invention, EMM-11, under suitable organic compound conversion conditions effective to convert at least 1 wt. % of the organic compound.

In its active form EMM-11 may exhibit a high acid activity, which may be measured with the alpha test. Alpha value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an alpha value of 1 (Rate Constant=0.016 sec$^{-1}$). The alpha test is described in U.S. Pat. No. 3,354,078; in the *Journal of Catalysis* 4, 527 (1965); 6, 278 (1966); and 61, 395 (1980), each incorporated herein by reference as to that description. The experimental conditions of the alpha test when used herein include a constant temperature of 538° C. and a variable flow rate as described in detail in the *Journal of Catalysis* 61, 395 (1980).

When used as a catalyst, EMM-11 may be intimately combined with a hydrogenating component such as tungsten, vanadium, molybdenum, rhenium, nickel, cobalt, chromium, manganese, or a noble metal such as, but not limited to, platinum or palladium where a hydrogenation-dehydrogenation function is to be performed. Such component may be in the composition by way of co-crystallization, exchanged into the composition to the extent a Group IIIA element, e.g., aluminum, is in the structure, impregnated therein or intimately physically admixed therewith. Such component may be impregnated in or on to it such as, for example, by, in the case of platinum, treating EMM-11 with a solution containing a platinum metal-containing ion. Thus, suitable platinum compounds for this purpose include chloroplatinic acid, platinous chloride and various compounds containing the platinum amine complex.

An absorbent comprising EMM-11 may be used in absorptive processes. In one or more embodiments, the invention includes a method of removing a solute from a gas or a liquid comprising the step of contacting an absorbent (in dehydrated on non-dehydrated form) comprising one or more embodiments of the synthetic crystalline microporous material of this invention, EMM-11, under suitable absorptive conditions effective to remove at least a portion of the solute from the gas or liquid.

In one or more embodiments, EMM-11 may be used for organic compound conversion and/or absorptive processes, including, but not limited to, selective molecular separation based on size and polar properties; as an ion-exchanger; as a catalyst in organic conversion reactions, such as cracking, hydrocracking, disproportionation, alkylation, isomerization, oxidation and synthesis of monoalkylamine and dialkylamines; as a chemical carrier; in gas chromatography; and in the petroleum industry to remove normal paraffins from distillates.

Binder Materials

As in the case of many catalysts, it may be desirable to incorporate EMM-11 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with EMM-11, i.e., combined therewith or present during synthesis of EMM-11, which is active, tends to change the conversion and/or selectivity of the catalyst in certain organic conversion processes. Inactive materials suitably serve as diluents to control the amount of conversion in a given process so that products may be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which may be composited with EMM-11 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays may be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, EMM-11 may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of EMM-11 (as a finely divided synthetic crystalline microporous material) and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented.

EXAMPLES

Example 1

Synthesis of EMM-11

Figure 3:
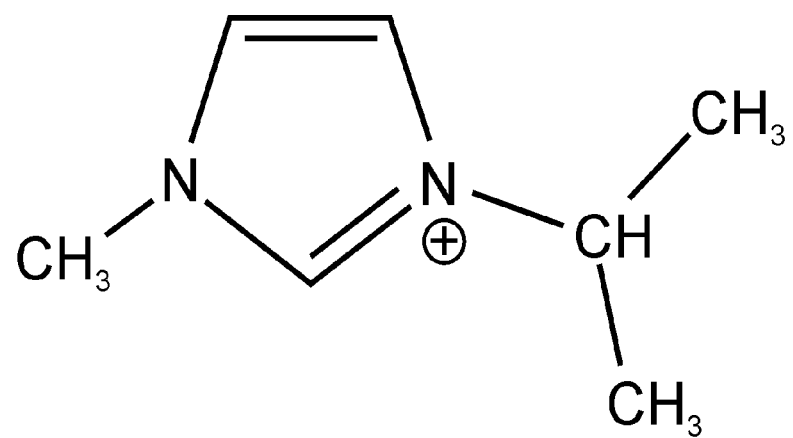
FIG. 3 is a representation of 3 isopropyl-1-methyl-1H-imidazol-3-ium, the organic SDA used in the Examples.

A germanium containing gel was prepared, according to the following description: 2.33 g of germanium oxide were dissolved in 39.07 g of a solution of 20.3 wt. % 3-isopropyl-1-methyl-1H-imidazol-3-ium hydroxide (FIG. 3). Then, 18.59 g of tetraethylorthosilicate were hydrolyzed in that solution and the mixture was left to evaporate under stirring until complete evaporation of the ethanol formed was achieved and the weight of the gel reached 34.5 g. Finally, 2.32 g of 48 wt. % HF solution was mixed in. The final composition of the gel was:

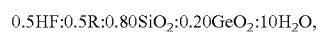

$0.5HF:0.5R:0.80SiO_2:0.20GeO_2:10H_2O$, where R is 3-isopropyl-1-methyl-1H-imidazol-3-ium. The mixture was transferred to Teflon-lined stainless steel autoclave and heated with tumbling (20 rpm) for 4 days at 160° C. The sample was washed with deionized water, dried in an air oven at 115° C. and then subjected to powder X-ray diffraction (XRD), which showed the product to be EMM-11 with a minor impurity.

Figure 4:
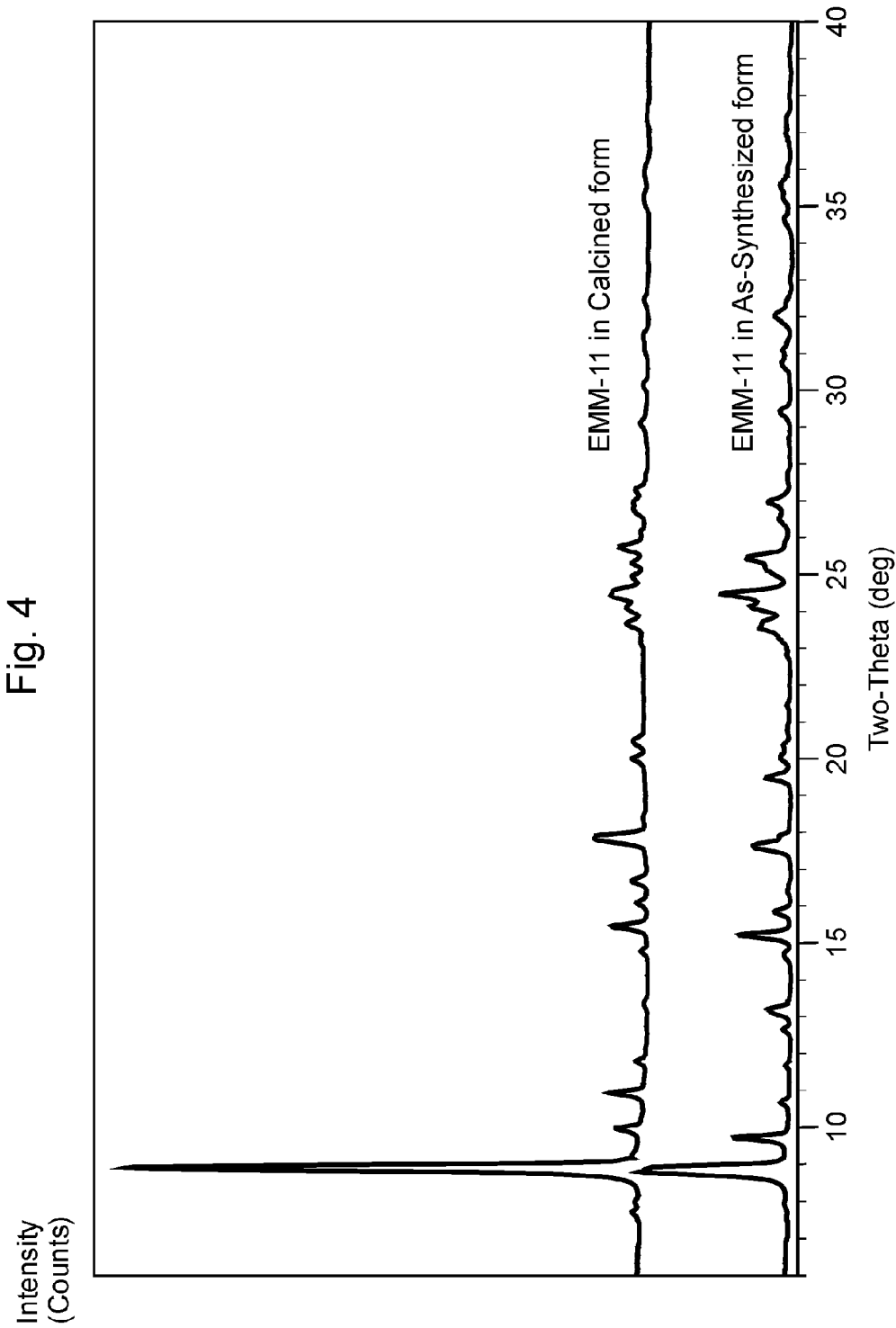
FIG. 4 displays the XRD pattern of EMM-11 produced in Example 1 in as-synthesized form and in calcined form.

The powder X-ray diffractograms of the sample as made and calcined (first in nitrogen atmosphere for 15 min. at 400° C. then in air for 2 hours at 600° C.) is shown in plots 4-A and 4-B, respectively, in FIG. 4. The position of the XRD reflection lines are given in Table 6 for the as-synthesized sample. The position of the XRD reflection lines are given in Table 7 for the calcined sample. The XRD reflection lines and XRD pattern of the calcined sample indicate that EMM-11 is stable to calcination.

TABLE 6

XRD Reflection Lines for EMM-11 of Example 1 in As-synthesized Form

| 2-Theta | d-spacing (Angstroms) | Relative Intensity |
|---|---|---|
| 8.85 | 9.99 | 100 |
| 9.71 | 9.10 | 21 |
| 10.66 | 8.29 | 4 |
| 11.68 | 7.57 | 2 |
| 13.18 | 6.71 | 14 |
| 14.69 | 6.03 | 6 |
| 15.21 | 5.820 | 21 |
| 15.84 | 5.589 | 8 |
| 16.53 | 5.358 | 2 |
| 17.64 | 5.025 | 26 |
| 17.88 | 4.957 | 11 |
| 19.49 | 4.550 | 11 |
| 20.04 | 4.427 | 16 |
| 20.33 | 4.364 | 10 |
| 21.45 | 4.139 | 2 |
| 23.57 | 3.772 | 31 |
| 23.67 | 3.756 | 39 |
| 24.46 | 3.637 | 58 |
| 25.22 | 3.528 | 51 |
| 25.43 | 3.499 | 42 |
| 26.54 | 3.356 | 13 |
| 26.96 | 3.304 | 24 |
| 29.42 | 3.034 | 6 |
| 30.75 | 2.905 | 12 |
| 31.08 | 2.875 | 10 |
| 31.27 | 2.860 | 5 |
| 32.02 | 2.793 | 15 |
| 32.36 | 2.765 | 7 |
| 34.65 | 2.587 | 7 |
| 35.24 | 2.545 | 24 |
| 35.58 | 2.521 | 18 |
| 36.11 | 2.486 | 2 |
| 36.98 | 2.429 | 7 |
| 37.35 | 2.406 | 7 |
| 39.15 | 2.299 | 2 |

TABLE 7

XRD Reflection Lines for EMM-11
of Example 1 in Calcined Form

| 2-Theta | d-spacing (Angstroms) | Relative Intensity |
|---|---|---|
| 8.90 | 9.92 | 100 |
| 9.96 | 8.88 | 5 |
| 10.92 | 8.10 | 6 |
| 11.79 | 7.50 | 2 |
| 13.34 | 6.63 | 1 |
| 14.77 | 5.993 | 1 |
| 15.45 | 5.732 | 7 |
| 16.09 | 5.506 | 2 |
| 16.69 | 5.309 | 3 |
| 17.84 | 4.969 | 16 |
| 20.00 | 4.436 | 3 |
| 20.47 | 4.334 | 3 |
| 23.67 | 3.755 | 5 |
| 24.11 | 3.689 | 10 |
| 24.48 | 3.633 | 17 |
| 24.93 | 3.569 | 2 |
| 25.33 | 3.513 | 3 |
| 25.73 | 3.459 | 7 |
| 26.12 | 3.409 | 1 |
| 26.94 | 3.306 | 9 |
| 27.28 | 3.266 | 6 |
| 29.11 | 3.065 | 5 |
| 30.15 | 2.962 | 3 |
| 31.15 | 2.869 | 5 |
| 31.47 | 2.840 | 5 |
| 32.45 | 2.757 | 4 |
| 33.73 | 2.655 | 2 |
| 35.26 | 2.543 | 6 |
| 35.88 | 2.501 | 3 |

Example 2

Synthesis of EMM-11

A germanium containing gel was prepared, according to the following description: 4.31 g of germanium oxide were dissolved in 43.3 g of a solution of 20.3 wt. % 3-isopropyl-1-methyl-1H-imidazol-3-ium hydroxide (FIG. 3). Then, 12.39 g of duPont LUDOX AS-40 colloidal silica was added and the mixture was left to evaporate under stirring until the weight of the gel reached 39 g. Finally, 2.58 g of 48 wt. % HF solution was mixed in. The final composition of the gel was:

$$0.5HF{:}0.5R{:}0.67\ SiO_2{:}0.33\ GeO_2{:}10H_2O,$$

where R is 3-isopropyl-1-methyl-1H-imidazol-3-ium. The mixture was transferred to Teflon-lined stainless steel autoclave and heated with tumbling (20 rpm) for 4 days at 160° C. The sample was washed with deionized water, dried in an air over at 115° C. and then subjected to powder X-ray diffraction (not shown), which showed the product to be EMM-11 with a minor impurity.

All patents, patent applications, test procedures (such as ASTM methods), priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A method for converting an organic compound comprising the step of contacting the organic compound with a catalyst comprising a synthetic crystalline microporous material under suitable organic compound conversion conditions effective to convert at least 1 wt. % of the organic compound, said synthetic crystalline microporous material comprising a framework of tetrahedrally-coordinated atoms (T-atoms) connected by bridging atoms, the framework of tetrahedrally-coordinated atoms (T-atoms) defined by connecting the tetrahedrally-coordinated atoms (T-atoms) in its unit cell having x, y and z coordinate positions in units of Angstroms in the range substantially as set forth in Table 6 below and having coordination sequence substantially as set forth in Table 7 below:

TABLE 6

| T-atom | Connected to: | x (Angstroms) | y (Angstroms) | z (Angstroms) |
|---|---|---|---|---|
| T1 | T2, T6, T13, T17 | 1.027 ± 1.00 | 1.469 ± 0.50 | 7.056 ± 0.50 |
| T2 | T1, T5, T14, T18 | 1.817 ± 1.00 | 1.469 ± 0.50 | 1.044 ± 0.50 |
| T3 | T4, T8, T15, T19 | 8.864 ± 1.00 | 6.032 ± 0.50 | 7.056 ± 0.50 |
| T4 | T3, T7, T16, T20 | 8.074 ± 1.00 | 6.032 ± 0.50 | 1.044 ± 0.50 |
| T5 | T2, T6, T9, T21 | 18.756 ± 1.00 | 1.469 ± 0.50 | 1.816 ± 0.50 |
| T6 | T1, T5, T10, T22 | 17.966 ± 1.00 | 1.469 ± 0.50 | 7.828 ± 0.50 |
| T7 | T4, T8, T11, T23 | 10.918 ± 1.00 | 6.032 ± 0.50 | 1.816 ± 0.50 |
| T8 | T3, T7, T12, T24 | 11.708 ± 1.00 | 6.032 ± 0.50 | 7.828 ± 0.50 |
| T9 | T5, T10, T14, T21 | 18.756 ± 1.00 | 6.032 ± 0.50 | 1.816 ± 0.50 |
| T10 | T6, T9, T13, T22 | 17.966 ± 1.00 | 6.032 ± 0.50 | 7.828 ± 0.50 |
| T11 | T7, T12, T16, T23 | 10.918 ± 1.00 | 1.469 ± 0.50 | 1.816 ± 0.50 |
| T12 | T8, T11, T15, T24 | 11.708 ± 1.00 | 1.469 ± 0.50 | 7.828 ± 0.50 |
| T13 | T1, T10, T14, T17 | 1.027 ± 1.00 | 6.032 ± 0.50 | 7.056 ± 0.50 |
| T14 | T2, T9, T13, T18 | 1.817 ± 1.00 | 6.032 ± 0.50 | 1.044 ± 0.50 |
| T15 | T3, T12, T16, T19 | 8.864 ± 1.00 | 1.469 ± 0.50 | 7.056 ± 0.50 |
| T16 | T4, T11, T15, T20 | 8.074 ± 1.00 | 1.469 ± 0.50 | 1.044 ± 0.50 |
| T17 | T1, T13, T18, T21 | 1.486 ± 1.00 | 3.751 ± 0.50 | 5.061 ± 0.50 |
| T18 | T2, T14, T17, T20 | 3.352 ± 1.00 | 3.751 ± 0.50 | 2.482 ± 0.50 |
| T19 | T3, T15, T20, T23 | 8.405 ± 1.00 | 3.751 ± 0.50 | 5.061 ± 0.50 |
| T20 | T4, T16, T18, T19 | 6.540 ± 1.00 | 3.751 ± 0.50 | 2.482 ± 0.50 |
| T21 | T5, T9, T17, T22 | 18.296 ± 1.00 | 3.751 ± 0.50 | 3.810 ± 0.50 |
| T22 | T6, T10, T21, T24 | 16.431 ± 1.00 | 3.751 ± 0.50 | 6.390 ± 0.50 |
| T23 | T7, T11, T19, T24 | 11.378 ± 1.00 | 3.751 ± 0.50 | 3.810 ± 0.50 |
| T24 | T8, T12, T22, T23 | 13.243 ± 1.00 | 3.751 ± 0.50 | 6.390 ± 0.50 |

TABLE 7

| T-atom Type | Label | Coordination Sequence | | | | | |
|---|---|---|---|---|---|---|---|
| 1 | T1 | 4 | 9 | 18 | 34 | 60 | 87 | 107 |
| 2 | T2 | 4 | 9 | 18 | 36 | 60 | 84 | 106 |
| 3 | T17 | 4 | 12 | 21 | 33 | 54 | 83 | 116 |
| 4 | T18 | 4 | 12 | 25 | 37 | 51 | 79 | 117 |

| T-atom Type | Label | Coordination Sequence | | | | | |
|---|---|---|---|---|---|---|---|
| 1 | T1 | 132 | 181 | 238 | 276 | 313 | 377 |
| 2 | T2 | 135 | 181 | 235 | 278 | 318 | 376 |
| 3 | T17 | 151 | 181 | 220 | 275 | 331 | 383 |
| 4 | T18 | 152 | 182 | 220 | 275 | 337 | 390. |

2. The method for converting an organic compound of claim 1, wherein said tetrahedrally-coordinated atoms (T-atoms) of said synthetic crystalline microporous material comprises one or more elements selected from the group consisting of B, Li, Be, Al, P, Si, Ga, Ge, Zn, Cr, Mg, Fe, Co, Ni, Mn, As, In, Cu, Sn, Sb, Ti, and Zr, and wherein said bridging atoms comprises one or more elements selected from the group consisting of O, N, F, S, Se, and C.

3. The method for converting an organic compound of claim 1, wherein said synthetic crystalline microporous material has a composition of:

$$aF:xR:XO_2:yY_2O_3:zH_2O,$$

wherein F is a compound that contains fluorine; R is an organic compound; X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; a is a number having a value in the range of greater than or equal to 0 to less than or equal to 0.4; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

4. The method for converting an organic compound of claim 3, wherein said organic compound of said synthetic crystalline material comprises 3-isopropyl-1-methyl-1H-imidazol-3-ium.

5. The method for converting an organic compound of claim 1, wherein said synthetic crystalline material, as synthesized, has an X-ray diffraction pattern including the peaks as substantially as set forth in Table 8 below:

TABLE 8

| d-spacing (Angstroms) | Relative Intensity |
|---|---|
| 10.1-9.9 | 60-100 |
| 9.20-9.01 | 5-50 |
| 5.86-5.78 | 5-50 |
| 5.05-5.00 | 5-50 |
| 3.79-3.76 | 20-70 |
| 3.77-3.74 | 20-70 |
| 3.65-3.62 | 30-80 |
| 3.54-3.51 | 30-80 |
| 3.51-3.49 | 20-70 |
| 3.32-3.29 | 5-50 |
| 2.552-2.538 | 5-50. |

6. The method for converting an organic compound of claim 5, wherein said synthetic crystalline microporous material has a composition of:

$$aF:xR:XO_2:yY_2O_3:zH_2O,$$

wherein F is a compound that contains fluorine; R is an organic compound; X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; a is a number having a value in the range of greater than or equal to 0 to less than or equal to 0.4; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

7. The method for converting an organic compound of claim 6, wherein said organic compound of said synthetic crystalline microporous material comprises 3-isopropyl-1-methyl-1H-imidazol-3-ium.

8. The method for converting an organic compound of claim 1, wherein said synthetic crystalline microporous material, as calcined, has an X-ray diffraction pattern including the peaks as substantially set forth in Table 9 below:

TABLE 9

| d-spacing (Angstroms) | Relative Intensity |
|---|---|
| 10.0-9.8 | 60-100 |
| 8.17-8.02 | 1-20 |
| 5.77-5.69 | 1-20 |
| 5.00-4.94 | 5-40 |
| 3.70-3.67 | 5-40 |
| 3.65-3.62 | 5-40 |
| 3.47-3.45 | 1-20 |
| 3.32-3.29 | 1-20 |
| 3.28-3.25 | 1-20 |
| 2.550-2.536 | 1-20. |

9. The method for converting an organic compound of claim 8, wherein said synthetic crystalline microporous material has a composition of:

$$XO_2:yY_2O_3:zH_2O,$$

wherein X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; y is a number having a value in the range of greater than or equal to 0 to less than or equal to 0.2; and z is a number having a value in the range of greater than or equal to 0 to less than or equal to 20.

10. The method for converting an organic compound of claim 1, wherein said synthetic crystalline microporous material is made by a process comprising the steps of:
(a) forming a reaction mixture comprising at least one element having tetrahedrally-coordinated atoms, an organic compound, and optionally at least one source of fluorine, wherein said at least one element having tetrahedrally-coordinated atoms is selected from the group consisting of B, Li, Be, Al, P, Si, Ga, Ge, Zn, Cr, Mg, Fe, Co, Ni, Mn, As, In, Cu, Sn, Sb, Ti, and Zr and is tetravalent, or a combination of tetravalent and trivalent, wherein said organic compound comprises 3-isopropyl-1-methyl-1H-imidazol-3-ium;
(b) maintaining said reaction mixture under suitable crystallization conditions effective to form crystals of said synthetic crystalline material; and
(c) recovering said crystals from said reaction mixture.

11. A method of removing a solute from a gas or a liquid comprising the step of contacting an absorbent comprising said synthetic crystalline microporous material of claim 1 under suitable absorptive conditions effective to remove at least a portion of said solute from said gas or liquid, said synthetic crystalline microporous material comprising a framework of tetrahedrally-coordinated atoms (T-atoms) connected by bridging atoms, said framework of tetrahedrally-coordinated atoms (T-atoms) defined by connecting said tetrahedrally-coordinated atoms (T-atoms) in its unit cell having x, y and z coordinate positions in units of Angstroms in the range substantially as set forth in Table 10 below and having coordination sequence substantially as set forth in Table 11 below:

TABLE 10

| T-atom | Connected to: | x (Angstroms) | y (Angstroms) | z (Angstroms) |
|---|---|---|---|---|
| T1 | T2, T6, T13, T17 | 1.027 ± 1.00 | 1.469 ± 0.50 | 7.056 ± 0.50 |
| T2 | T1, T5, T14, T18 | 1.817 ± 1.00 | 1.469 ± 0.50 | 1.044 ± 0.50 |
| T3 | T4, T8, T15, T19 | 8.864 ± 1.00 | 6.032 ± 0.50 | 7.056 ± 0.50 |
| T4 | T3, T7, T16, T20 | 8.074 ± 1.00 | 6.032 ± 0.50 | 1.044 ± 0.50 |
| T5 | T2, T6, T9, T21 | 18.756 ± 1.00 | 1.469 ± 0.50 | 1.816 ± 0.50 |
| T6 | T1, T5, T10, T22 | 17.966 ± 1.00 | 1.469 ± 0.50 | 7.828 ± 0.50 |
| T7 | T4, T8, T11, T23 | 10.918 ± 1.00 | 6.032 ± 0.50 | 1.816 ± 0.50 |
| T8 | T3, T7, T12, T24 | 11.708 ± 1.00 | 6.032 ± 0.50 | 7.828 ± 0.50 |
| T9 | T5, T10, T14, T21 | 18.756 ± 1.00 | 6.032 ± 0.50 | 1.816 ± 0.50 |
| T10 | T6, T9, T13, T22 | 17.966 ± 1.00 | 6.032 ± 0.50 | 7.828 ± 0.50 |
| T11 | T7, T12, T16, T23 | 10.918 ± 1.00 | 1.469 ± 0.50 | 1.816 ± 0.50 |
| T12 | T8, T11, T15, T24 | 11.708 ± 1.00 | 1.469 ± 0.50 | 7.828 ± 0.50 |
| T13 | T1, T10, T14, T17 | 1.027 ± 1.00 | 6.032 ± 0.50 | 7.056 ± 0.50 |
| T14 | T2, T9, T13, T18 | 1.817 ± 1.00 | 6.032 ± 0.50 | 1.044 ± 0.50 |
| T15 | T3, T12, T16, T19 | 8.864 ± 1.00 | 1.469 ± 0.50 | 7.056 ± 0.50 |
| T16 | T4, T11, T15, T20 | 8.074 ± 1.00 | 1.469 ± 0.50 | 1.044 ± 0.50 |
| T17 | T1, T13, T18, T21 | 1.486 ± 1.00 | 3.751 ± 0.50 | 5.061 ± 0.50 |
| T18 | T2, T14, T17, T20 | 3.352 ± 1.00 | 3.751 ± 0.50 | 2.482 ± 0.50 |
| T19 | T3, T15, T20, T23 | 8.405 ± 1.00 | 3.751 ± 0.50 | 5.061 ± 0.50 |
| T20 | T4, T16, T18, T19 | 6.540 ± 1.00 | 3.751 ± 0.50 | 2.482 ± 0.50 |
| T21 | T5, T9, T17, T22 | 18.296 ± 1.00 | 3.751 ± 0.50 | 3.810 ± 0.50 |
| T22 | T6, T10, T21, T24 | 16.431 ± 1.00 | 3.751 ± 0.50 | 6.390 ± 0.50 |
| T23 | T7, T11, T19, T24 | 11.378 ± 1.00 | 3.751 ± 0.50 | 3.810 ± 0.50 |
| T24 | T8, T12, T22, T23 | 13.243 ± 1.00 | 3.751 ± 0.50 | 6.390 ± 0.50 |

TABLE 11

| T-atom Type | Label | Coordination Sequence | | | | | | | | | | | |
|---|---|---|---|---|---|---|---|---|---|---|---|---|---|
| 1 | T1 | 4 | 9 | 18 | 34 | 60 | 87 | 107 | 132 | 181 | 238 | 276 | 313 | 377 |
| 2 | T2 | 4 | 9 | 18 | 36 | 60 | 84 | 106 | 135 | 181 | 235 | 278 | 318 | 376 |
| 3 | T17 | 4 | 12 | 21 | 33 | 54 | 83 | 116 | 151 | 181 | 220 | 275 | 331 | 383 |
| 4 | T18 | 4 | 12 | 25 | 37 | 51 | 79 | 117 | 152 | 182 | 220 | 275 | 337 | 390. |

12. The method of removing a solute from a gas or a liquid of claim 11, wherein said tetrahedrally-coordinated atoms (T-atoms) of said synthetic crystalline microporous material comprise one or more elements selected from the group consisting of B, Li, Be, Al, P, Si, Ga, Ge, Zn, Cr, Mg, Fe, Co, Ni, Mn, As, In, Cu, Sn, Sb, Ti, and Zr, and wherein said bridging atoms comprise one or more elements selected from the group consisting of O, N, F, S, Se, and C.

13. The method of removing a solute from a gas or a liquid of claim 11, wherein said synthetic crystalline microporous material having a composition of:

$$aF:xR:XO_2:yY_2O_3:zH_2O,$$

wherein F is a compound that contains fluorine; R is an organic compound; X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; a is a number having a value in the range of greater than or equal to 0 to less than or equal to 0.4; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

14. The method of removing a solute from a gas or a liquid of claim 13, wherein said organic compound of said synthetic crystalline material comprises 3-isopropyl-1-methyl-1H-imidazol-3-ium.

15. The method of removing a solute from a gas or a liquid of claim 11, wherein said synthetic crystalline material, as synthesized, has an X-ray diffraction pattern including the peaks as substantially as set forth in Table 12 below:

TABLE 12

| d-spacing (Angstroms) | Relative Intensity |
|---|---|
| 10.1-9.9 | 60-100 |
| 9.20-9.01 | 5-50 |
| 5.86-5.78 | 5-50 |
| 5.05-5.00 | 5-50 |
| 3.79-3.76 | 20-70 |
| 3.77-3.74 | 20-70 |
| 3.65-3.62 | 30-80 |
| 3.54-3.51 | 30-80 |
| 3.51-3.49 | 20-70 |
| 3.32-3.29 | 5-50 |
| 2.552-2.538 | 5-50. |

16. The method of removing a solute from a gas or a liquid of claim 15, wherein said synthetic crystalline microporous material has a composition of:

$$aF:xR:XO_2:yY_2O_3:zH_2O,$$

wherein F is a compound that contains fluorine; R is an organic compound; X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; a is a number having a value in the range of greater than or equal to 0 to less than or equal to 0.4; x is a number having a value in the range of greater than or equal to 0 to less than or equal to 0.4; y is a number having a value in the range of greater than or equal to 0 to less than or equal to 0.2; and z is a number having a value in the range of greater than or equal to 0 to less than or equal to 20.

17. The method of removing a solute from a gas or a liquid of claim 16, wherein said organic compound of said synthetic crystalline microporous material comprises 3-isopropyl-1-methyl-1H-imidazol-3-ium.

18. The method of removing a solute from a gas or a liquid of claim 11, wherein said synthetic crystalline microporous material, as calcined, has an X-ray diffraction pattern including the peaks as substantially set forth in Table 13 below:

TABLE 13

| d-spacing (Angstroms) | Relative Intensity |
|---|---|
| 10.0-9.8 | 60-100 |
| 8.17-8.02 | 1-20 |
| 5.77-5.69 | 1-20 |
| 5.00-4.94 | 5-40 |
| 3.70-3.67 | 5-40 |
| 3.65-3.62 | 5-40 |
| 3.47-3.45 | 1-20 |
| 3.32-3.29 | 1-20 |
| 3.28-3.25 | 1-20 |
| 2.550-2.536 | 1-20. |

19. The method of removing a solute from a gas or a liquid of claim 18, wherein said synthetic crystalline microporous material has a composition of:

$$XO_2 : yY_2O_3 : zH_2O,$$

wherein X is one or more elements capable of tetrahedral coordination selected from the group consisting of Li, Be, P, Si, Ge, Zn, Cr, Mg, Co, Ni, Mn, As, In, Cu, Sn, Sb, Ti, and Zr; Y is one or more trivalent elements capable of tetrahedral coordination selected from the group consisting of B, Al, Fe, and Ga; y is a number having a value in the range of greater than or equal to 0 to less than or equal to 0.2; and z is a number having a value in the range of greater than or equal to 0 to less than or equal to 20.

20. The method of removing a solute from a gas or a liquid of claim 11, wherein said synthetic crystalline microporous material is made by a process comprising the steps of:
 (a) forming a reaction mixture comprising at least one element having tetrahedrally-coordinated atoms, an organic compound, and optionally at least one source of fluorine, wherein said at least one element having tetrahedrally-coordinated atoms is selected from the group consisting of B, Li, Be, Al, P, Si, Ga, Ge, Zn, Cr, Mg, Fe, Co, Ni, Mn, As, In, Cu, Sn, Sb, Ti, and Zr and is tetravalent, or a combination of tetravalent and trivalent, wherein said organic compound comprises 3-isopropyl-1-methyl-1H-imidazol-3-ium;
 (b) maintaining said reaction mixture under suitable crystallization conditions effective to form crystals of said crystalline material; and
 (c) recovering said crystals from said reaction mixture.

* * * * *